(12) United States Patent
Hacker

(10) Patent No.: US 9,091,682 B1
(45) Date of Patent: Jul. 28, 2015

(54) TISSUE SPECIMEN BOTTLE WITH COLOR INDICATOR IN LID VERIFYING AND CONFIRMING PRESENCE OF HUMAN TISSUE OR BLOOD CONTAINED IN SPECIMEN BOTTLE

(71) Applicant: Steven M Hacker, Delray Beach, FL (US)

(72) Inventor: Steven M Hacker, Delray Beach, FL (US)

( * ) Notice: Subject to any disclaimer, the term of this patent is extended or adjusted under 35 U.S.C. 154(b) by 0 days.

(21) Appl. No.: 14/267,037

(22) Filed: May 1, 2014

(51) Int. Cl.
*C12Q 1/04* (2006.01)
*G01N 33/52* (2006.01)

(52) U.S. Cl.
CPC .................... *G01N 33/523* (2013.01)

(58) Field of Classification Search
USPC ......................................... 604/317, 374, 375
See application file for complete search history.

(56) References Cited

U.S. PATENT DOCUMENTS

| | | | |
|---|---|---|---|
| 4,035,150 A | 7/1977 | Jaffe | |
| 4,045,291 A | 8/1977 | Berger | |
| 4,063,894 A | 12/1977 | Ogawa et al. | |
| 4,260,393 A | 4/1981 | Gibson | |
| 4,277,250 A | 7/1981 | Melnick et al. | |
| 4,297,271 A | 10/1981 | Guthlein et al. | |
| 4,386,053 A | 5/1983 | Motobayashi | |
| 4,541,987 A | 9/1985 | Guadagno | |
| 4,562,043 A | 12/1985 | Mennen | |
| 4,578,358 A | 3/1986 | Oksman et al. | |
| 4,578,359 A | 3/1986 | Oksman et al. | |
| D284,215 S | 6/1986 | Sherwin et al. | |
| 4,676,950 A | 6/1987 | Foster | |
| 4,725,553 A | 2/1988 | Guadagno | |
| 5,043,142 A | 8/1991 | Ichikawa et al. | |
| 5,081,040 A | 1/1992 | Patel et al. | |
| 5,310,680 A | 5/1994 | Baker et al. | |
| 5,318,894 A | 6/1994 | Pugia | |
| 5,424,040 A | 6/1995 | Bjornsson | |
| 6,258,327 B1 | 7/2001 | Tatum | |
| 6,344,335 B1 * | 2/2002 | Tausk et al. | 435/7.1 |
| 6,409,970 B1 | 6/2002 | Phifer | |
| 6,410,336 B1 | 6/2002 | Augurt | |
| 6,468,474 B2 | 10/2002 | Bachand et al. | |
| 7,517,691 B2 | 4/2009 | Waldenburg | |
| 8,053,203 B2 | 11/2011 | Wan et al. | |
| 8,062,901 B2 | 11/2011 | Dai et al. | |
| 8,349,573 B2 | 1/2013 | Wan et al. | |
| 8,389,287 B2 | 3/2013 | Chandler | |

FOREIGN PATENT DOCUMENTS

| | | | |
|---|---|---|---|
| EP | 2182371 | * | 5/2010 |
| EP | 2372373 | * | 5/2011 |

* cited by examiner

*Primary Examiner* — Ralph Gitomer

(57) ABSTRACT

A method and apparatus for visually confirming and verifying the presence of human tissue or blood in a tissue specimen collection bottle and includes a test pad that inserts into the undersurface of a lid of a specimen bottle which undergoes a chromogenic reaction confirming the presence of human tissue or blood in said specimen bottle.

9 Claims, 4 Drawing Sheets

FIGURE 4
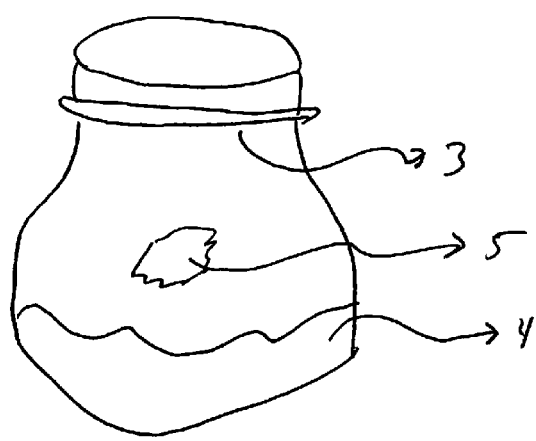
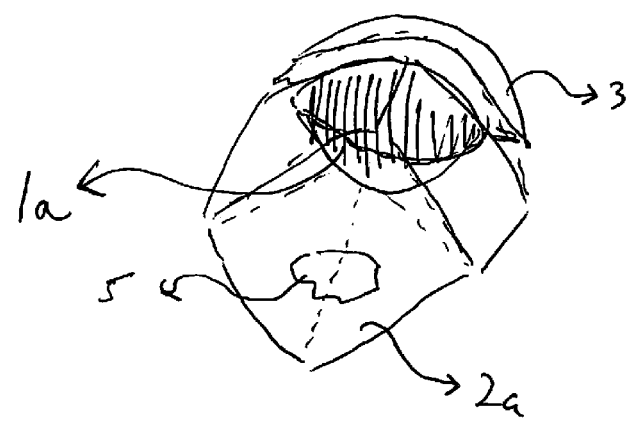
Figure 4a

TISSUE SPECIMEN BOTTLE WITH COLOR INDICATOR IN LID VERIFYING AND CONFIRMING PRESENCE OF HUMAN TISSUE OR BLOOD CONTAINED IN SPECIMEN BOTTLE

FIELD OF INVENTION

The present invention relates to a method and apparatus for visually confirming and verifying the presence of human tissue or blood in a specimen collection bottle by a surgeon. More specifically, the method employs a chromogenic test pad inserted into the undersurface of a lid of a clear specimen bottle and together the pad and lid is used as a visual indices tool which may be visualized through a clear tissue specimen bottle to confirm to the surgeon the placement of tissue in the bottle.

BACKGROUND OF THE INVENTION

The present invention relates to a method and apparatus for visually confirming and verifying the presence of human tissue or blood in a specimen collection bottle by a surgeon. More specifically, the method employs a chromogenic test pad inserted into the undersurface of a lid of a clear specimen bottle and together the pad and lid is used as a visual indices tool which may be visualized through a clear tissue specimen bottle to confirm to the surgeon the placement of tissue in the bottle.

It is common practice for physicians and surgeons after removing human tissue from the body to place such tissue in a specimen collection bottle containing fixative to enable processing of such tissue so that a pathologist may render a diagnosis of such tissue. During the rush of surgery or rapid pace outpatient and inpatient biopsies the surgeon may forget to place the tissue into the specimen bottle, unknowingly lose the specimen, or small specimens are accidentally disposed of after they are thought to have been placed into a specimen bottle. Further, the physician or surgical team may not carefully examine the specimen bottle to ensure and confirm that his staff had placed the specimen in the tissue collection bottle or the submitted specimen is so small it may be difficult to visualize its presence in the bottle. As a result, the pathology labs, not infrequently, receive a specimen bottle with no tissue inside.

Prior Art, is focused entirely on testing stool for the presence of occult blood and many methods including U.S. Pat. No. 4,725,553, U.S. Pat. No. 2,838,377, U.S. Pat. No. 3,996,006, U.S. Pat. No. 4,175,923 describe various methods of a test to detect occult blood in stool using guaiac paper or guaiac substitutes and or various activating substances. However, none of the prior art, deals with employing guaiac paper or substitute guaiac paper as a novel apparatus contained within the lid of pathology specimen collection bottles and more specifically employed to detect and confirm the presence of human tissue or blood within a pathology specimen bottle.

Accordingly, an apparatus and methodology which overcomes the shortcomings of prior common practice is desired such that surgeon or surgical team can quickly examine a tissue bottle to verify and confirm that human tissue or blood was placed in the bottle. It is the broad object of this invention to reduce the likelihood of lost tissue specimens, misplaced human tissue, or blood samples and avoid a physician or surgeon accidentally submitting empty tissue specimen bottles by creating a visual verification system utilizing the lid of a specimen bottle to serve as an indicator for surgeons in order for surgical staff to quickly visualize the inside of the specimen bottle to confirm presence of human tissue in bottle by noting a color change in the undersurface of the lid by looking through the bottom of a clear specimen bottle.

BRIEF SUMMARY OF THE INVENTION

The present invention relates to a method and apparatus for visually confirming and verifying the presence of human tissue or blood in a specimen collection bottle by a surgeon. More specifically, the method employs a chromogenic test pad inserted into the undersurface of a lid of a clear specimen bottle and together the pad and lid is used as a visual indices tool which may be visualized through a clear tissue specimen bottle to confirm to the surgeon the placement of tissue in the bottle. The test pad may consist of a variety of known chromogenic substances that may include a variety of known activating substances to effect a color change in the presence of human tissue or blood but preferably would contain a solid peroxygen compound and a solid guaiac substitute reagent preferably consisting of guaiacolsulfonate and the peroxygen compound would be potassium monopersulfate as previously described in U.S. Pat. No. 4,725,553 obviating the need for the use of additional reagent materials or activating solutions.

BRIEF DESCRIPTION OF THE DRAWINGS

The various features of the present invention and the manner of attaining them will be described in greater detail with reference to the following description, claims, drawings, wherein reference numerals are reused, where appropriate to indicate a correspondence between the referenced items, and wherein the preferred embodiments of the invention will herein after be described in conjunction with appended drawings to illustrate and not to limit the invention wherein like designations denote like elements and in which:

FIG. 4 and FIG. 4a is an isometric and a cross section bottom view respectively of a tissue specimen bottle containing fixative and also the lid with the test pad inserted into its undersurface showing the color change of test pad as a result of human tissue inserted into bottle.

DETAILED DESCRIPTION OF THE PREFERRED EMBODIMENT

Figure 1:
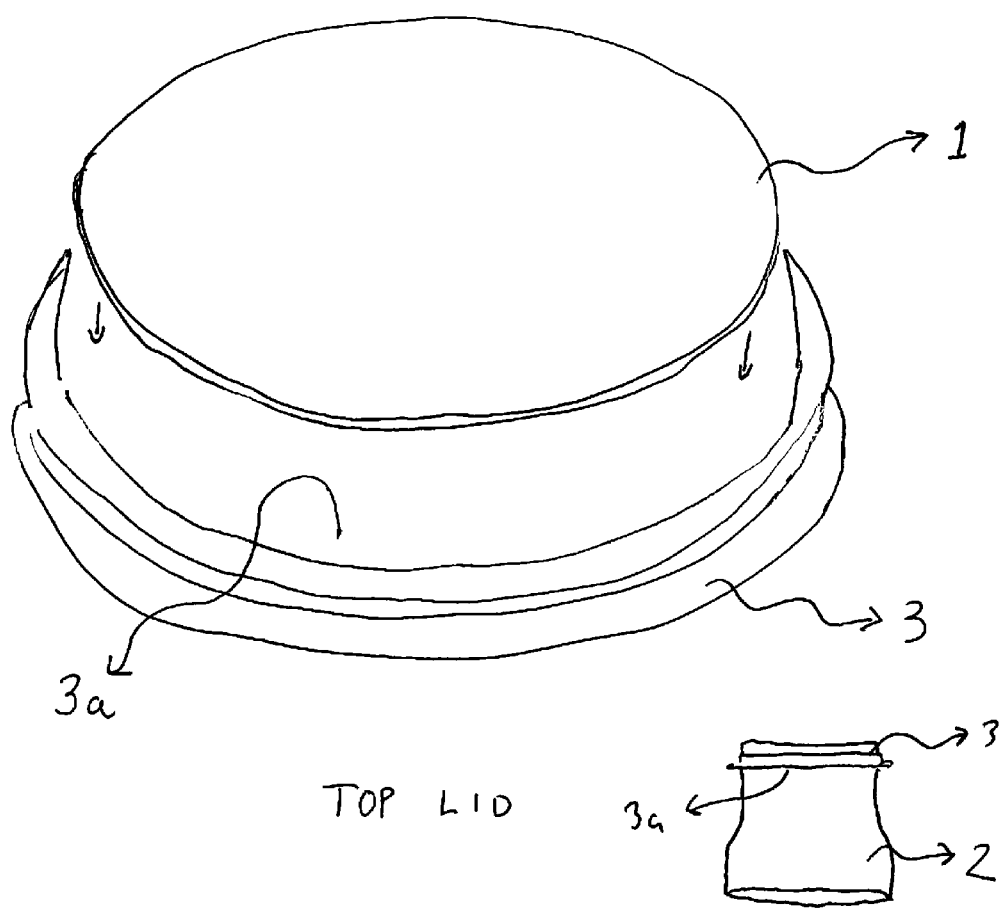
FIG. 1 is a assembled isometric view of the preferred absorbent test pad positioned over the inside of undersurface of lid.

Referring now to FIG. 1, the preferred absorbent test pad is shown to include test pad 1 that in its preferred mode is a dry test pad cut in the shape to fit into the undersurface of the lid 3a of a clear specimen tissue collection bottle 2 with a lid 3. The test pad 1 is shown overlying and not yet inserted into the undersurface of the lid 3a and may consist of a variety of known chromogenic substances that may or may not require a variety of known activating substances to effect a color change in the presence of human tissue or blood but preferably would contain a solid peroxygen compound and a solid guaiac substitute reagent.

Figure 2:
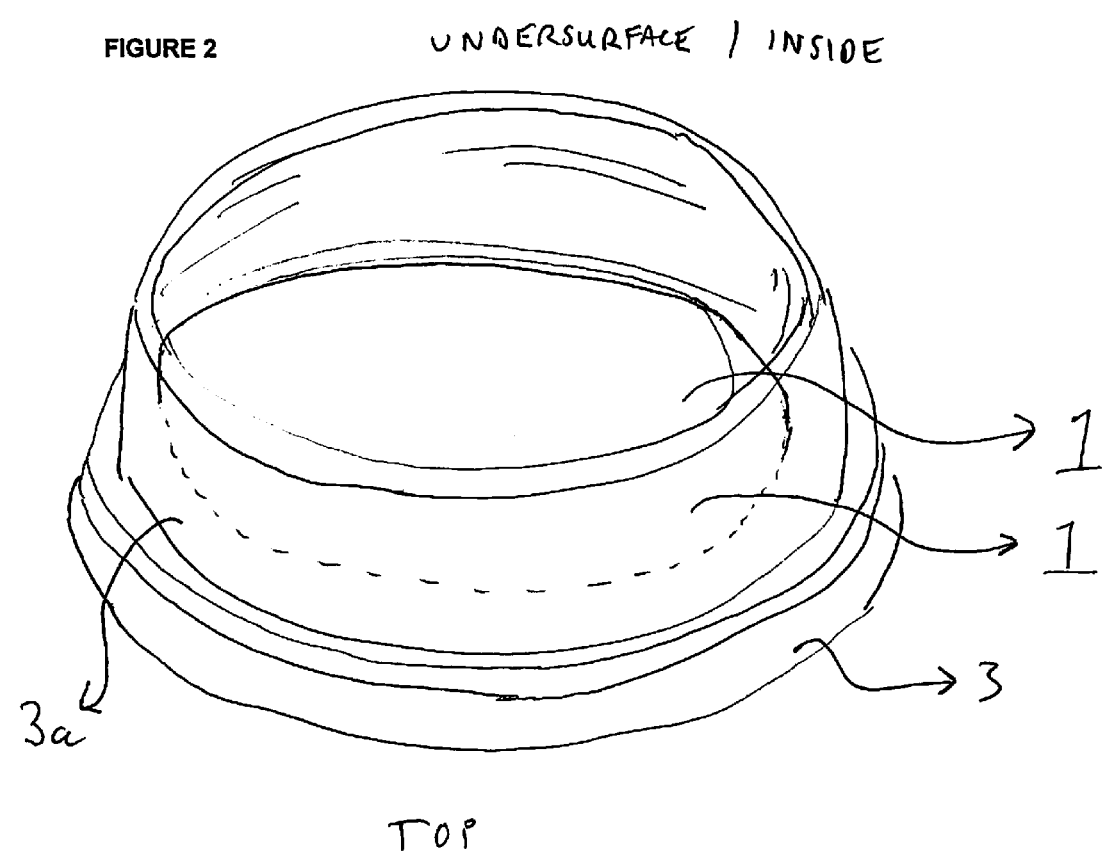
FIG. 2 is a assembled cross sectional undersurface view of the lid of a specimen bottle containing the preferred absorbent test pad inserted to its undersurface; and FIG. 3

Referring now to FIG. 2, the lid of a specimen bottle 3 is shown with the test pad 1 inserted into the undersurface of the lid 3a so that it is snug and a part of the undersurface and inside of the lid of the specimen bottle 3.

Figure 3:
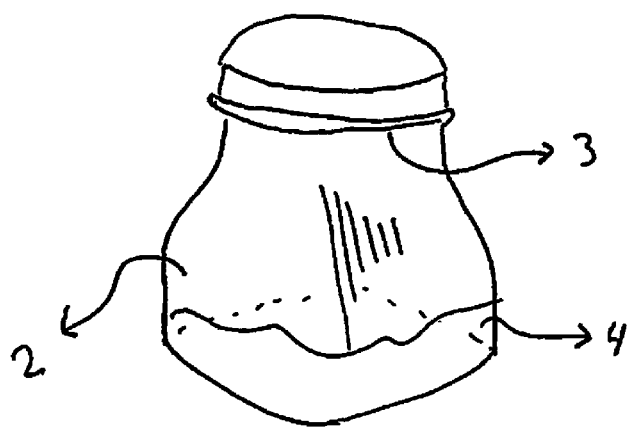
FIG. 3a is an isometric view and a cross section bottom view respectively of an empty tissue specimen bottle containing fixative and also the lid with the test pad inserted into its undersurface.
Figure 3:
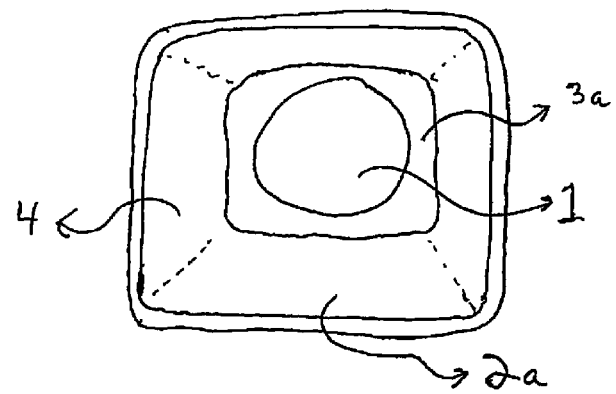

Referring to FIG. 3, the bottle 2 is an isometric view and FIG. 3a is a cross sectional bottom view in its empty state of human tissue or blood but still containing a transparent fixative 4 so that viewing through the bottom of the specimen bottle 2a may be demonstrated to see an unchanged test pad 1 on the undersurface of the lid 3a.

Referring to FIG. 4, an isometric view and FIG. 4a a cross sectional view of specimen bottle 2 such that human tissue or blood 5 is initially placed into the specimen bottle by the surgical team after being harvested from the body and the test pad may be exposed to human tissue and blood in the specimen bottle upon agitating the bottle shortly after placement of human tissue or blood in the bottle. After a member of the surgical team agitates the specimen bottle to effect the tissue or blood contacting the test pad 1, the surgical team may perform a visual inspection utilizing a cross sectional bottom view of tissue specimen bottle 2 containing fixative 4 and also the lid with the test pad inserted into its undersurface enabling viewing through the inside of the bottle and effecting the chromogenic color change of test pad 1a as a result of contact with human tissue or blood inserted into bottle.

While this invention has been particularly shown and described in reference to the preferred embodiments thereof, it would be understood by those skilled in the art that various changes in form and detail may be made therein without departing from the scope and spirit of the invention encompassed by the impended claims. Although the embodiments have been described in reference to a test pad and specimen collection bottle, the assembly, system and method according to the embodiments of the present invention may also apply to any chromogenic test pad inserted into the lid or any portion of a collection bottle, that would enable a physician or surgical team to view the chromogenic color change through the collection bottle to confirm the presence of a chromogenic color change or there may be a test pad or ingredient in the bottle that requires the addition of activating solutions to the specimen bottle to effect a color change. The scope of the invention also extends to various combinations and modifications that may fall within the spirit of the appended claim.

Object of Invention

The main object of the present invention is to provide a method and apparatus for visually confirming and verifying the presence of human tissue or blood in a tissue specimen collection bottle and includes a test pad that inserts into the undersurface of a lid of a specimen bottle which undergoes a chromogenic reaction in a fixative solution confirming the presence of human tissue or blood in said specimen bottle.

Another object of the present invention is to provide a human tissue or blood specimen bottle that can provide a visual color change and verification process to a surgical team confirming presence of human tissue or blood in specimen bottle.

REFERENCES

U.S. Pat. No. 4,725,553,
U.S. Pat. No. 2,838,377,
U.S. Pat. No. 3,996,006,
U.S. Pat. No. 4,175,923

What is claimed as new and desired to be protected by Letters Patent of the United States is:

1. A verification method for confirming the presence of tissue in a tissue specimen bottle comprising:
   a. providing a specimen bottle with a lid that has a chromogenic test pad in a bottom portion of the lid which can contact contents of the specimen bottle, wherein the test pad changes color in the presence of tissue,
   b. contacting the contents of the specimen bottle with the bottom portion of the lid,
   c. determining if a color change has occurred in the test pad,
   d. correlating a color change in the test pad with the presence of tissue in the specimen bottle and no color change with the absence of tissue in the specimen bottle.

2. The method of claim 1 wherein said test pad comprises a sheet of absorbent paper.

3. The method of claim 1 wherein the specimen bottle comprises a clear specimen bottle.

4. The method of claim 1 wherein further the test pad changes color in the presence of blood.

5. The method of claim 4, wherein the test pad comprises a guaiac compound and a peroxygen compound.

6. The method of claim 5 wherein the guaiac compound comprises guaiacolsulfonate.

7. The method of claim 5 wherein the guaiac compound comprises guaiacolsulfonate and the peroxygen compound comprises potassium monopersulfate.

8. The method of claim 5 wherein the peroxygen compound comprises a solid peroxygen compound.

9. The method of claim 8 wherein the peroxygen compound comprises potassium monopersulfate.

\* \* \* \* \*